US011459498B2

(12) United States Patent
Moloney et al.

(10) Patent No.: US 11,459,498 B2
(45) Date of Patent: Oct. 4, 2022

(54) ALKYL LACTONE-DERIVED CORROSION INHIBITORS

(71) Applicant: ChampionX USA Inc., Sugar Land, TX (US)

(72) Inventors: Jeremy Moloney, Katy, TX (US); Jeremy Wayne Bartels, Sugar Land, TX (US); Jeffrey M. Servesko, Bend, OR (US)

(73) Assignee: ChampionX USA Inc., Sugar Land, TX (US)

(*) Notice: Subject to any disclaimer, the term of this patent is extended or adjusted under 35 U.S.C. 154(b) by 0 days.

(21) Appl. No.: 17/234,601

(22) Filed: Apr. 19, 2021

(65) Prior Publication Data
US 2021/0246360 A1 Aug. 12, 2021

Related U.S. Application Data

(62) Division of application No. 16/507,649, filed on Jul. 10, 2019, now Pat. No. 11,008,500.

(60) Provisional application No. 62/697,165, filed on Jul. 12, 2018.

(51) Int. Cl.
| | |
|---|---|
| *C09K 8/54* | (2006.01) |
| *C07C 69/675* | (2006.01) |
| *C07C 235/10* | (2006.01) |
| *C09K 8/524* | (2006.01) |
| *C09K 15/22* | (2006.01) |
| *C23F 11/14* | (2006.01) |

(52) U.S. Cl.
CPC ............. *C09K 8/54* (2013.01); *C07C 69/675* (2013.01); *C07C 235/10* (2013.01); *C09K 8/524* (2013.01); *C09K 15/22* (2013.01); *C23F 11/145* (2013.01)

(58) Field of Classification Search
CPC .......... C09K 8/54; C09K 8/524; C09K 15/22; C09K 2208/32; C09K 8/035; C07C 69/675; C07C 235/10; C23F 11/145; C23F 11/128
See application file for complete search history.

(56) References Cited

U.S. PATENT DOCUMENTS

| | | | | |
|---|---|---|---|---|
| 2,923,738 | A | * | 2/1960 | Williams ................ C11D 1/523 564/201 |
| 3,062,631 | A | * | 11/1962 | Thompson ............ C10L 1/2493 508/222 |
| 3,436,463 | A | * | 4/1969 | Williams ............. A61K 31/165 514/408 |
| 3,821,678 | A | | 6/1974 | Eley |
| 3,831,678 | A | * | 8/1974 | Mondshine ........... E21B 36/003 166/288 |
| 3,832,367 | A | * | 8/1974 | Heiba ................... C07C 233/16 510/502 |
| 3,989,637 | A | | 11/1976 | Hogue et al. |
| 4,167,514 | A | | 9/1979 | Brois et al. |
| 4,179,392 | A | * | 12/1979 | Heiba ................... C07C 59/185 510/502 |
| 4,263,014 | A | | 4/1981 | Davis et al. |
| 4,828,740 | A | * | 5/1989 | Farng ................... C10M 139/00 558/294 |
| 4,866,142 | A | | 9/1989 | Gutierrez et al. |
| 4,963,275 | A | | 10/1990 | Gutierrez et al. |
| 5,055,230 | A | | 10/1991 | Clubley et al. |
| 5,237,090 | A | | 8/1993 | Swarup et al. |
| 6,054,514 | A | | 4/2000 | Kulkarni |
| 6,368,552 | B1 | | 4/2002 | Shimura et al. |
| 6,583,213 | B1 | | 6/2003 | Fawkes et al. |
| 7,105,628 | B2 | | 9/2006 | Kuntimaddi et al. |
| 8,859,675 | B2 | | 10/2014 | Richards et al. |
| 11,008,500 | B2 | * | 5/2021 | Moloney ............... C07C 69/675 |
| 2010/0041857 | A1 | * | 2/2010 | Harris ................... C07C 235/10 528/292 |
| 2010/0069541 | A1 | | 3/2010 | Thetford et al. |
| 2015/0299628 | A1 | | 10/2015 | Choi et al. |
| 2016/0122619 | A1 | | 5/2016 | Lucente-Schultz et al. |
| 2017/0009101 | A1 | | 1/2017 | Yasui |
| 2017/0260409 | A1 | | 9/2017 | Thetford et al. |
| 2017/0306504 | A1 | | 10/2017 | Moloney |

FOREIGN PATENT DOCUMENTS

| | | | |
|---|---|---|---|
| CA | 1240669 | 8/1988 | |
| CN | 105022237 A | 11/2015 | |
| CN | 106046868 A | 10/2016 | |
| EP | 0491538 A1 * | 6/1992 | ........... C07C 271/22 |
| EP | 0491538 | 6/1993 | |
| FR | 1224810 A * | 6/1960 | ........... C07C 235/10 |
| GB | 1095659 A * | 12/1967 | ............ C07C 67/44 |
| GB | 1520599 | 8/1978 | |
| JP | 2013129933 A | 7/2013 | |
| KR | 101830944 B1 | 2/2018 | |
| RU | 2217428 C2 | 11/2003 | |
| WO | 03054120 A1 | 7/2003 | |
| WO | WO-2004039865 A1 * | 5/2004 | ............ C08G 73/02 |
| WO | 2016180916 A1 | 11/2016 | |
| WO | 2020014328 A1 | 1/2020 | |

OTHER PUBLICATIONS

EIC Structure Search (Year: 2020).*
Tebbji et al. (2007) "The effect of some lactones as inhibitors for the corrosion of mild steel in 1 M hydrochloric acid", Materials Chemistry and Physics, vol. 106, Issue 2-3, pp. 260-267.
Jamalizadeh et al. (2009) "Quantum chemical studies on corrosion inhibition of some lactones on mild steel in acid media", Corrosion Science, 51(6):1428-1435.

(Continued)

*Primary Examiner* — Pamela H Weiss
(74) *Attorney, Agent, or Firm* — Kagan Binder, PLLC

(57) ABSTRACT

Disclosed are alkyl lactone-derived hydroxyamide and alkyl lactone-derived hydroxyester used in compositions and methods for inhibiting corrosion. The alkyl lactone-derived hydroxyamide and alkyl lactone-derived hydroxyester are reaction products of an alkyl lactone and an amine, and an alkyl lactone and an alcohol, respectively.

20 Claims, No Drawings

(56) References Cited

OTHER PUBLICATIONS

Khamis et al. (1991) "Acid Corrosion Inhibition of Nickel by 2-(Triphenosphoranylidene) Succinic Anhydride", Corrosion, 47(9): 677-686.
Broggini et al. (1991) "Synthesis of 5-hydroxymethyl-1,4-dioxan-2-one", Organic preparations and procedures international, 23(6):762-4.
Krevalis et al. (2006) "Investigation into the use of hydroxy-containing amides for oil flowable formulations", Journal of ASTM International, 3(1):293-303.
Detert et al. (1996) "Cationic amphiphiles with G-protein-stimulatory activity: Studies on the role of the basic domain in the activation process" Pharmazie, 2:67-72.
Goossen et al. (2010) "Silver triflate-catalysed synthesis of gamma-lactones from fatty acids", Green Chem., 12:197-200.
Miller et al. (2000) "5-HETE Congeners as Modulators of Cell Proliferation", Bioorganic & Medicinal Chemistry Letters, 10:1913-1916.
EIC Structure Search for U.S. Appl. No. 16/507,649 dated Dec. 29, 2020, 104 pages.
International Preliminary Report on Patentability for International Application No. PCT/US2019/041155, dated Jan. 21, 2021, 8 pages.
International Search Report and Written Opinion for International Application No. PCT/US2019/041152, dated Sep. 23, 2019, 6 pages.
International Preliminary Report on Patentability for International Application No. PCT/US2019/041152, dated Jan. 21, 2021, 9 pages.
International Search Report and Written Opinion for International Application No. PCT/US2019/041155, dated Oct. 25, 2019, 11 pages.

\* cited by examiner

ALKYL LACTONE-DERIVED CORROSION INHIBITORS

CROSS REFERENCE TO RELATED APPLICATIONS

This application is a divisional of U.S. application Ser. No. 16/507,649, filed Jul. 10, 2019, which claims the benefit of U.S. Provisional Patent Application Ser. No. 62/697,165, filed Jul. 12, 2018, the disclosures of which are incorporated by reference herein in their entireties.

FIELD OF THE INVENTION

The present application is directed at inhibition or prevention of corrosion in the oil and gas industry.

BACKGROUND

Corrosion of metal surfaces continues to be a problem in the oil and gas industry. Aqueous liquids are injected into the earth and recovered from the earth during subterranean hydrocarbon recovery processes such as hydraulic fracturing (fracking) and tertiary oil recovery. In one or more such processes, an aqueous liquid called an "injectate" is injected into a subterranean formation. Injectates include water, solids, solvents therein or both. In one or more such processes, a water source called "produced water," namely, water that flows back from the subterranean formation, is recovered and collected. Produced water includes one or more of injectate, connate (native water present in the subterranean formation along with the hydrocarbon), sea water, and minor (e.g. less than 5 wt %) amounts of hydrocarbon products, which are hydrocarbon liquids or solids entrained (dispersed, emulsified, or dissolved) in the produced water. The injectate and the produced water can include "corrodents" such as salts or other dissolved solids, liquids, gases, or combination thereof that cause, accelerate, or promote corrosion of metal containments that contact the corrodents. These aggressive constituents can cause severe corrosion as evidenced by surface pitting, embrittlement, and general loss of metal. Corrosion problems are even more troublesome in deep-sea operations where replacement of corroded equipment is difficult and costly. As a result, almost all operators in the oil and gas industry employ corrosion inhibitors to reduce corrosion in metal containments, which contact aqueous liquids containing corrodents.

Governmental regulations imposed on the oil and gas-producing industry have demanded "greener" chemistries with reduced environmental effects, yet requiring identical performance levels as with existing treatments.

In view of these challenges, improved, and in particular environmentally friendly, corrosion inhibitors are desirable.

SUMMARY

Described herein are compositions and methods for inhibiting corrosion in a fluid comprising water, gas, liquid hydrocarbon or combination thereof.

In one aspect of the invention is a composition comprising at least one alkyl lactone-derived hydroxyamide or alkyl lactone-derived hydroxyester to inhibit corrosion, the at least one alkyl lactone-derived hydroxyamide formed by a reaction between an alkyl lactone with an amine, and the alkyl lactone-derived hydroxyester formed by a reaction between an alkyl lactone with an alcohol.

In another aspect of the invention is a composition comprising: a fluid source; and the alkyl lactone-derived hydroxyamide or alkyl lactone-derived hydroxyester composition.

In yet another aspect of the invention is a method of inhibiting corrosion of metal containments in contact with a fluid source comprising the steps of:
introducing into the fluid source a composition comprising at least one alkyl lactone-derived hydroxyamide or alkyl lactone-derived hydroxyester, the at least one alkyl lactone-derived hydroxyamide formed by a reaction between an alkyl lactone with an amine, and the at least one alkyl lactone-derived hydroxyester formed by a reaction between an alkyl lactone with an alcohol.

The above-described compositions and methods are suitable for use in aquatic environments as they have lower toxicities.

DETAILED DESCRIPTION

Although the present disclosure provides references to various embodiments, persons skilled in the art will recognize that changes may be made in form and detail without departing from the spirit and scope of the invention. Various embodiments will be described in detail with reference to the figures. Reference to various embodiments does not limit the scope of the claims attached hereto. Additionally, any examples set forth in this specification are not intended to be limiting and merely set forth some of the many possible embodiments for the appended claims.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety.

As used herein, the term "alkyl" refers to a monovalent group derived by the removal of a single hydrogen atom from a straight or branched chain or cyclic saturated or unsaturated hydrocarbon containing from one to sixty carbon atoms.

As used herein, the term "corrodents," are materials that cause, initiate, catalyze, accelerate, induce, or otherwise promote the corrosion of metals.

As used herein, the term "corrosion inhibitor" (CI) means a compound or mixture that prevents, retards, mitigates, reduces, controls and/or delays corrosion.

As used herein, the term "fluid source" means any fluid used in oil or gas well production operations that contain one or more corrodents.

As used herein, the term "inhibits," "inhibiting," or grammatical equivalents thereof refer to preventing, retarding, mitigating, reducing, controlling and/or delaying corrosion.

As used herein, the term "injectate" means water plus any solids or liquids dispersed therein that is injected into a subterranean formation for the purpose of inducing hydrocarbon recovery therefrom. Injectates optionally include salts, polymers, surfactants, scale inhibitors, stabilizers, metal chelating agents, corrosion inhibitors, paraffin inhibitors, and other additives as determined by the operator in a subterranean hydrocarbon recovery process.

As used herein, the term "produced water" means water that flows back from a subterranean reservoir and is collected during a hydrocarbon recovery process including, but not limited to hydraulic fracturing and tertiary oil recovery. Produced water includes residual hydrocarbon products entrained therein and one or more of injectate, connate (native water present in the subterranean formation along with the hydrocarbon), brackish water, and sea water. Produced water ranges in temperature from about −30° C. to about 200° C., depending on the subterranean reservoir and the terranean environment and infrastructure proximal to the subterranean reservoir.

As used herein, the terms "comprise(s)," "include(s)," "having," "has," "can," "contain(s)," and variants thereof are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

As used herein, the term "optional" or "optionally" means that the subsequently described event or circumstance may but need not occur, and that the description includes instances where the event or circumstance occurs and instances in which it does not.

As used herein, the term "about" modifying, for example, the quantity of an ingredient in a composition, concentration, volume, process temperature, process time, yield, flow rate, pressure, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities. Further, where "about" is employed to describe a range of values, for example "about 1 to 5" the recitation means "1 to 5" and "about 1 to about 5" and "1 to about 5" and "about 1 to 5" unless specifically limited by context.

As used herein, the term "substantially" means "consisting essentially of" and includes "consisting of" "consisting essentially of" is construed as in U.S. patent law, and "consisting of" is construed as in U.S. patent law. For example, a solution that is "substantially free" of a specified compound or material may be free of that compound or material, or may have a minor amount of that compound or material present, such as through unintended contamination, side reactions, or incomplete purification. A "minor amount" may be a trace, an unmeasurable amount, an amount that does not interfere with a value or property, or some other amount as provided in context. A composition that has "substantially only" a provided list of components may consist of only those components, or have a trace amount of some other component present, or have one or more additional components that do not materially affect the properties of the composition. Additionally, "substantially" modifying, for example, the type or quantity of an ingredient in a composition, a property, a measurable quantity, a method, a value, or a range, employed in describing the embodiments of the disclosure, refers to a variation that does not affect the overall recited composition, property, quantity, method, value, or range thereof in a manner that negates an intended composition, property, quantity, method, value, or range. Where modified by the term "substantially" the claims appended hereto include equivalents according to this definition.

As used herein, any recited ranges of values contemplate all values within the range and are to be construed as support for claims reciting any sub-ranges having endpoints which are real number values within the recited range. By way of example, a disclosure in this specification of a range of from 1 to 5 shall be considered to support claims to any of the following ranges: 1-5; 1-4; 1-3; 1-2; 2-5; 2-4; 2-3; 3-5; 3-4; and 4-5.

Described are compositions and methods to inhibit corrosion of metal containments used in liquid hydrocarbon recovery, processing, transportation, and storage operations.

In embodiments, the compounds used in the compositions and methods for inhibiting corrosion are alkyl lactone-derived hydroxyamides, alkyl lactone derived-hydroxyesters, or combination thereof. The compounds are formed by the reaction of alkyl lactones and amines, or alkyl lactones and alcohols. Such alkyl lactone-derived compounds have the general formula shown below as formula I, wherein X=nitrogen or oxygen;

wherein $R^1$=any fatty tail derived from 1-30 carbon saturated or unsaturated alkyl group or a ring structure including cyclohexyl, cyclopentyl, phenyl, benzyl, or variants thereof;

wherein $R^2$=is H or any 1-10 carbon saturated or unsaturated alkyl group or a ring structure which would link to $R^3$; and wherein $R^3$=H or any 1-10 carbon saturated or unsaturated alkyl group or a ring structure which would link to $R^2$, e.g. pyrrolidine or azepane, and the like.

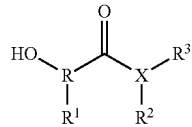

Formula I

In embodiments, the alkyl lactone-derived hydroxyamide is shown below as formula II, III and IV, with the various groups as previously described.

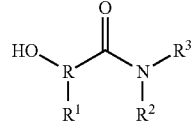

Formula II

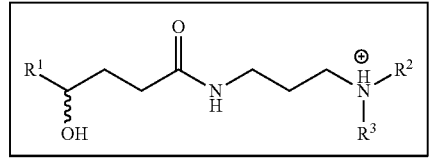

Formula III

-continued

Formula IV

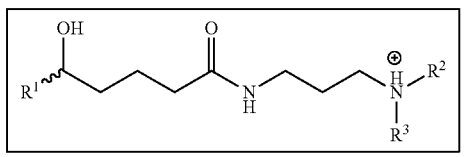

wherein, $R^1$=any fatty tail derived from 1-30 carbon atom saturated or unsaturated alkyl group or a ring structure including cyclohexyl, cyclopentyl, phenyl, benzyl, or variants thereof;

wherein $R^2$=H or any 1-10 carbon atom saturated or unsaturated alkyl group or being a ring structure which would link to $R^3$; and wherein $R^3$=H or any 1-10 carbon atom saturated or unsaturated alkyl group or being a ring structure which would link to $R^2$, e.g. pyrrolidine or azepane, and the like.

In embodiments, $R^2$ and $R^3$ are individually selected from isopropyl, butyl, pentyl, isobutyl or isopentyl groups. In embodiments, $R^2$ and $R^3$ individually may include one or more aminopropylamine chains such as dimethylaminopropylamine (DMAPA) or dibutylaminopropylamine (DBAPA). In embodiments, $R^2$=$R^3$. In embodiments, $R^2$ and $R^3$ are individually derived from the following amines:

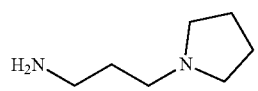

Aminopropyl pyrrolidine

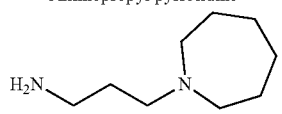

Aminopropyl azepane and

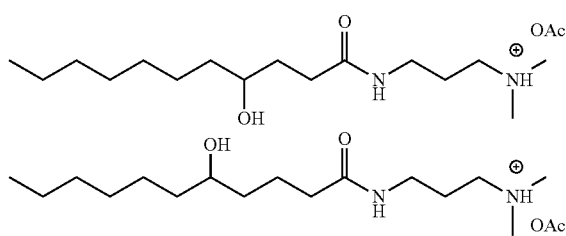

An extended dibutylaminopropylenediamine

In embodiments, the alkyl lactone-derived hydroxyamides include one or more of the following structures or a combination thereof:

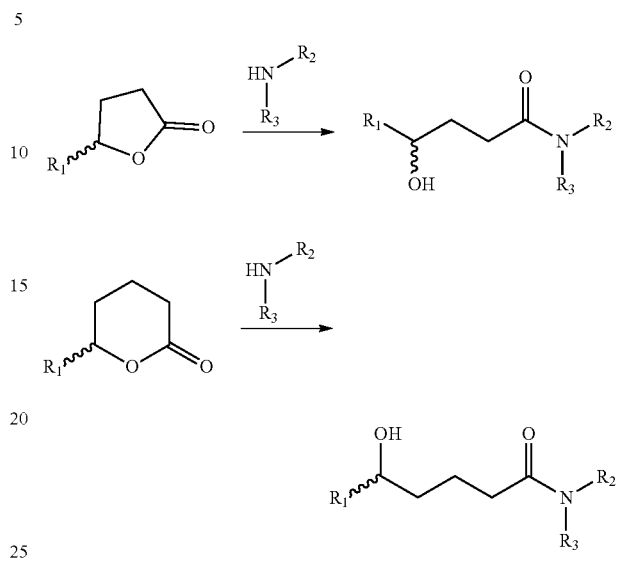

Any suitable method may be used to synthesize the alkyl lactone-derived hydroxyamides. The synthesis of the alkyl lactone-derived hydroxyamides is not limited by the described processes.

In embodiments, the alkyl lactone-derived hydroxyamides are obtained by reacting alkyl lactones with amines as shown below, wherein $R^1$ is an alkyl moiety and $R^2$ and $R^3$ are selected from H or an alkyl group, with, the proviso that only one of $R^2$ and $R^3$ may be H.

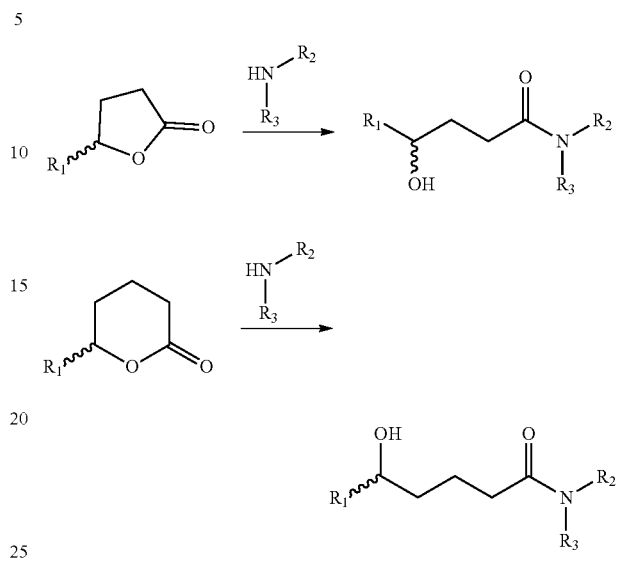

In embodiments, the alkyl lactone-derived hydroxyamide is formed by reacting an alkyl lactone and an aminopropyl amine followed by acidification as shown below, wherein, $R^1$=any fatty tail is derived from 1-30 carbon atom saturated or unsaturated alkyl group or a ring structure including cyclohexyl, cyclopentyl, phenyl, benzyl, or variants thereof; and wherein $R^2$ and $R^3$ are an H or an alkyl group with the proviso that only one of $R^2$ and $R^3$ may be H.

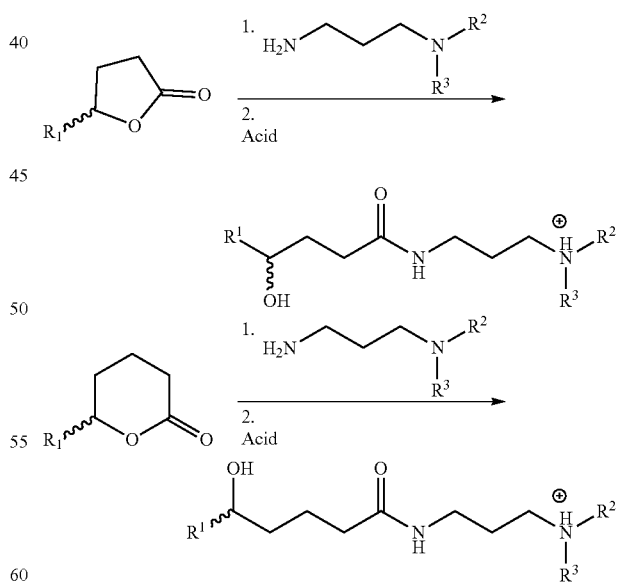

In embodiments, the alkyl lactone-derived hydroxyamide is formed by reacting the alkyl lactone, which is γ-undecalactone and an amine, which is dibutylaminopropylamine. The resultant alkyl lactone-derived hydroxyamide is followed by acidification with acetic acid:

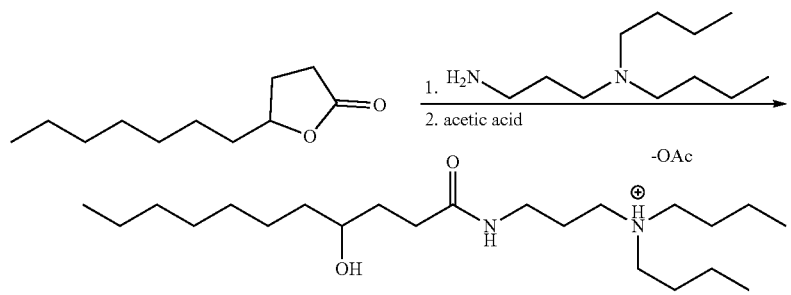

In embodiments, the alkyl lactone-derived hydroxyamide is the reaction product of γ-undecalactone with dibutylamine:

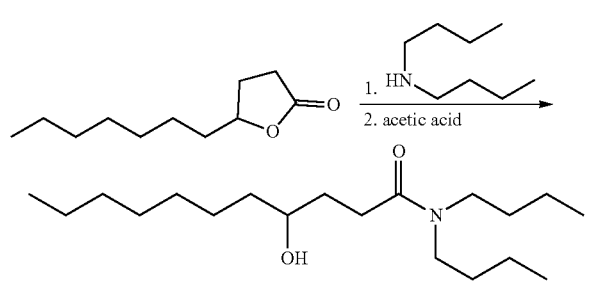

In embodiments, the alkyl lactone is γ-undecalactone reacted with dimethylaminopropyl amine (DMAPA) and acidified (e.g. acetic acid) as follows:

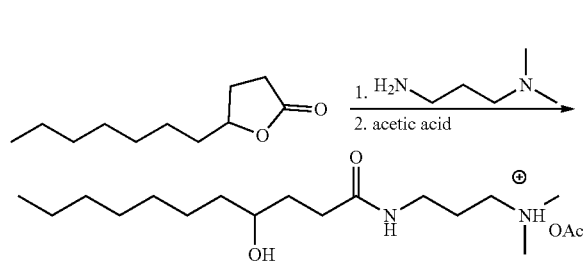

In embodiments, the alkyl lactone-derived hydroxyamide is a reaction product between δ undecalactone and DMAPA.

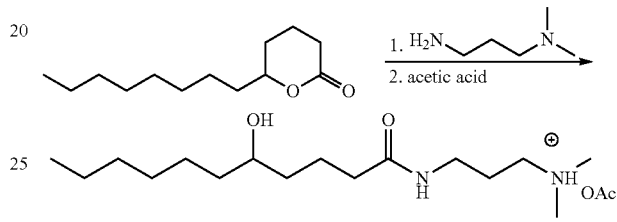

In embodiments, the alkyl lactone-derived hydroxyamide is a reaction product between γ octalactone and DMAPA:

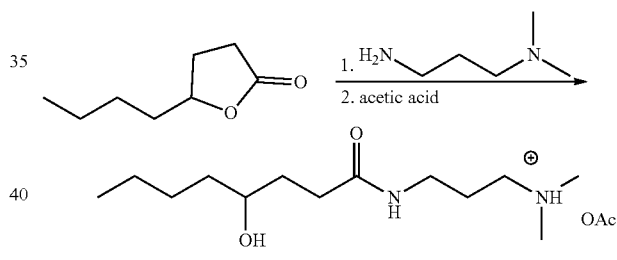

In other embodiments, the alkyl lactone-derived hydroxyamides are reaction products as shown below:

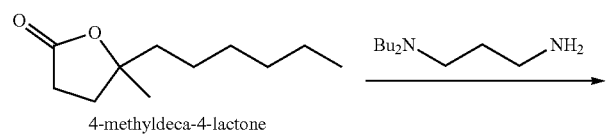

4-methyldeca-4-lactone

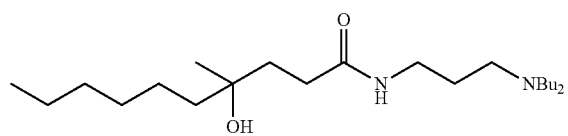

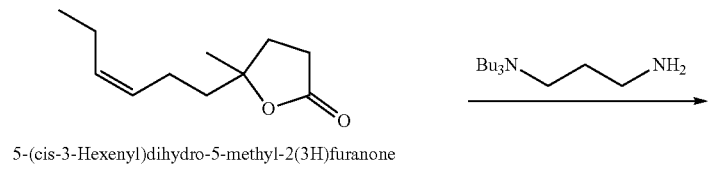

5-(cis-3-Hexenyl)dihydro-5-methyl-2(3H)furanone

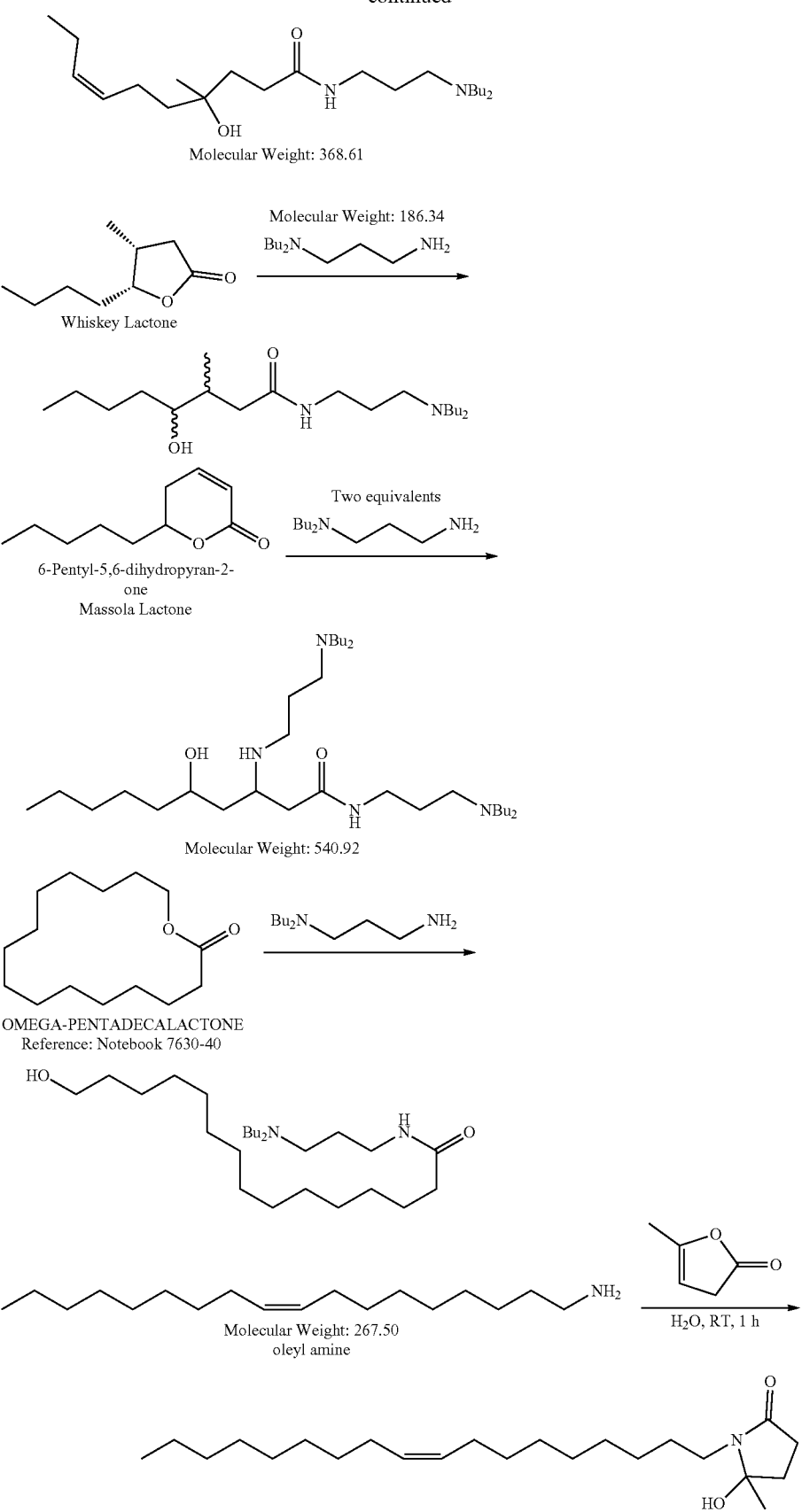

In some embodiments, the compositions and methods useful for inhibiting corrosion includes an alkyl lactone-derived hydroxyester. In embodiments, the alkyl lactone-derived hydroxyester is a reaction product of an alkyl lactone with an alcohol, and as shown below, wherein $R^1$ is an alkyl moiety (as described above), and $R^2$ is an alkyl group.

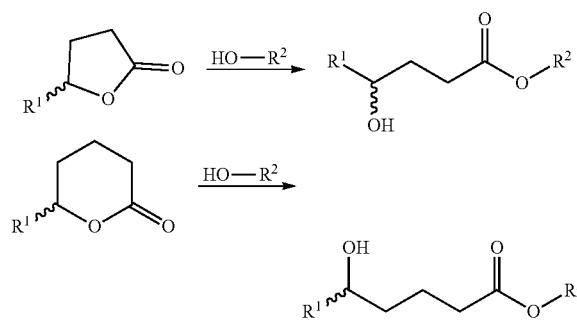

In embodiments, the alkyl lactone-derived hydroxyester is the reaction product of γ-undecalactone reacted with dibutylaminoethanol, followed by acidification to form the ammonium salt of the tertiary amino moiety:

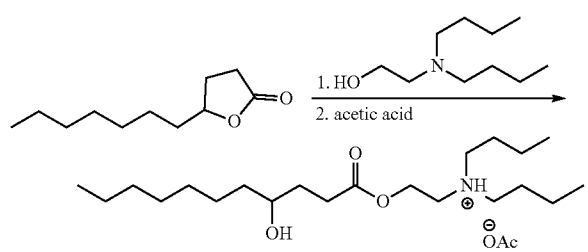

In embodiments, the hydroxyl of the alkyl lactone-derived hydroxyester or alkyl lactone-derived hydroxyamide can be further modified. In embodiments, the resultant hydroxyl is modified by displacing the hydrogen of the hydroxyl to form an O-bonded moiety. Suitable O-bonded moieties include ether, carboxylic acid, silyl ether, and the like. In embodiments, suitable O-bonded moieties are shown below, wherein $R^1$ is as described previously, and $R^4$ is alkyl, silyl, carboxyl, and the like.

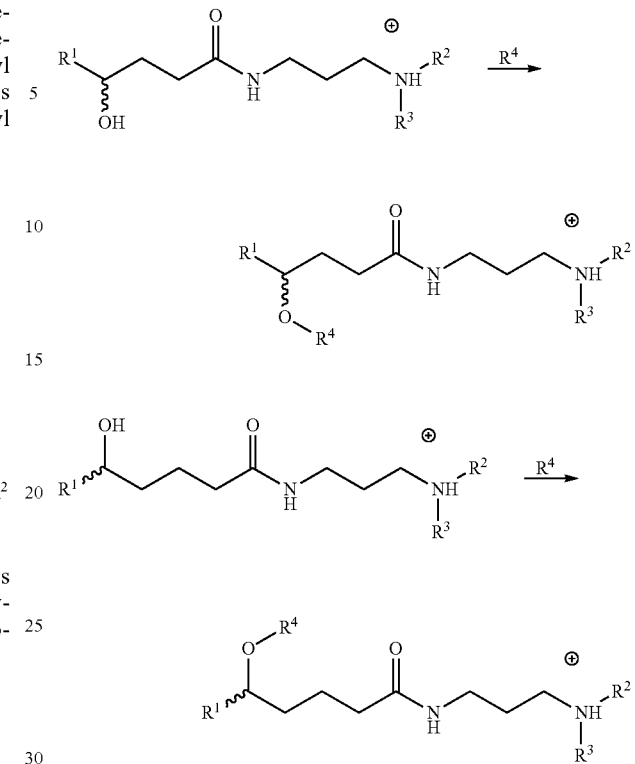

In embodiments, the O-bonded moiety is the reaction product of the alkyl lactone-derived hydroxyamide or alkyl lactone-derived hydroxyester with maleic anhydride or other anhydride moiety. For example, the alkyl lactone-derived hydroxyamide (which is a reaction between γ-undecalactone with dibutylaminopropylamine) is further reacted with maleic anhydride as follows:

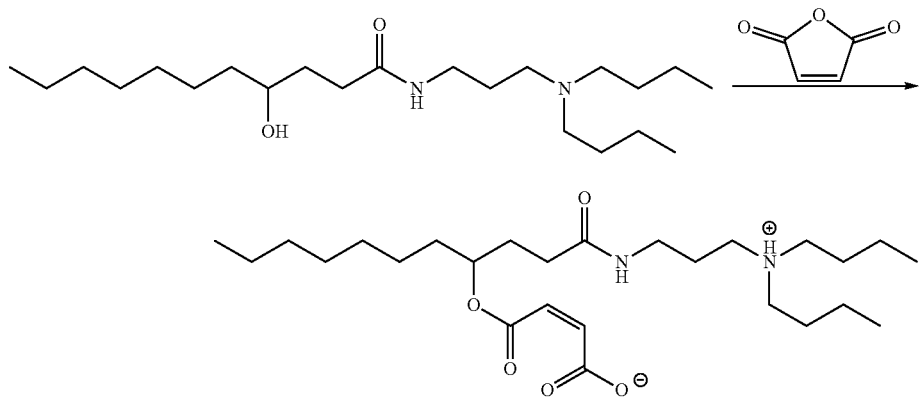

In embodiments, the ether is formed from the alkyl lactone-derived hydroxyamide by reacting with a bromide. In embodiments, the alkyl lactone-derived hydroxyamide is formed by reacting γ-undecalactone with DBAPA. The resultant alkyl lactone-derived hydroxyamide is further reacted with n-butyl bromide to yield a corresponding ether as follows:

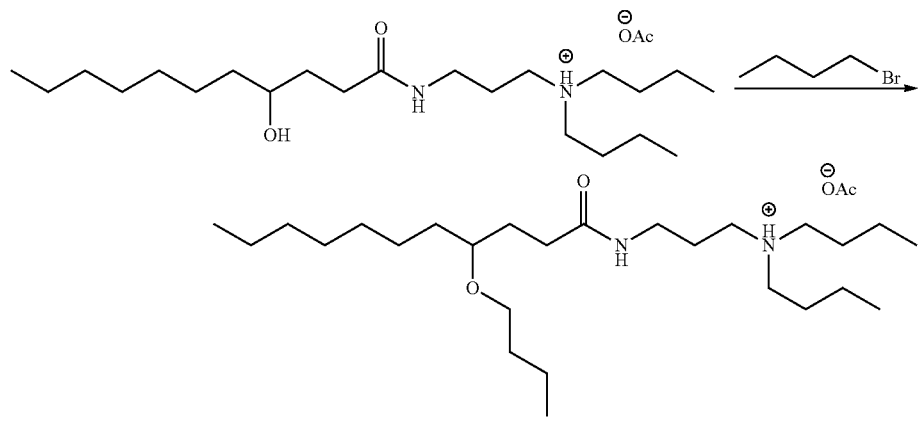

In still other embodiments, the resultant hydroxyl of the alkyl lactone-derived hydroxyamide or alkyl lactone-derived hydroxyester is modified by oxidation to a ketone. For example, oxidation to a ketone is as shown below, wherein $R^1$ is as described above, and the newly formed ketone can be left as-is or further reacted with amines (Schiff base formation, reductive amination, and the like), or reacted via aldol reactions, Mannich reactions, and the like.

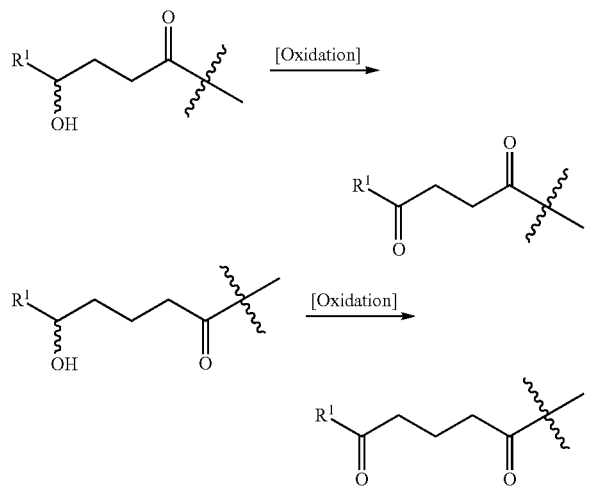

In embodiments, the oxidation can be with yridinium chlorochromate (PCC) to yield a ketone as shown below:

Any suitable alkyl lactones may be used to react with the amine. In embodiments, the alkyl lactones have at least two carbon atoms in the lactone ring. In embodiments, the lactones are from 2-30 or 5-20 carbon atoms. In embodiments, the alkyl lactones are gamma-alkyl lactones and delta-alkyl lactones. In embodiments, the alkyl lactones are beta, epsilon, or larger variants such as omega-alkyl lactones (for example co-pentadecalactone). In embodiments, the variability in the alkyl moiety are at the gamma or delta carbon, but can occur along the alpha, beta, gamma, delta, or epsilon position along the lactone ring, in multiple locations and chiralities.

In embodiments, the alkyl chain is a straight chain alkyl having 1-30 carbon straight or branched chain alkyl. In other embodiments, the alkyl chain is a branching, unsaturation or additional functionality. In embodiments, unsubstituted alkyl groups include methyl, ethyl, n-propyl, i-propyl, n-butyl, i-butyl, s-butyl, t-butyl, n-pentyl, i-pentyl, s-pentyl, t-pentyl, hexyl, heptyl, octyl, nonyl, decyl, lauryl, and the like.

In embodiments, the alkyl lactones are either synthetic or natural. In embodiments, the synthetic lactones can be produced from fatty acids plus acrylic acid and peroxide.

In embodiments, the lactones are naturally produced, where they are commonly used as food additives or flavor/fragrance molecules. In embodiments, natural lactones include cis-3-methyl-4-octanolide (whisky lactone), massoia lactone (6-Pentyl-5,6-dihydropyran-2-one), 5-(cis-3-Hexenyl)dihydro-5-methyl-2(3H)furanone, 4-methyldeca-4-lactone, angelica lactone and the like.

In embodiments, commercially available lactones, for example from Sigma Aldrich include 4-methyldeca-4-lac-

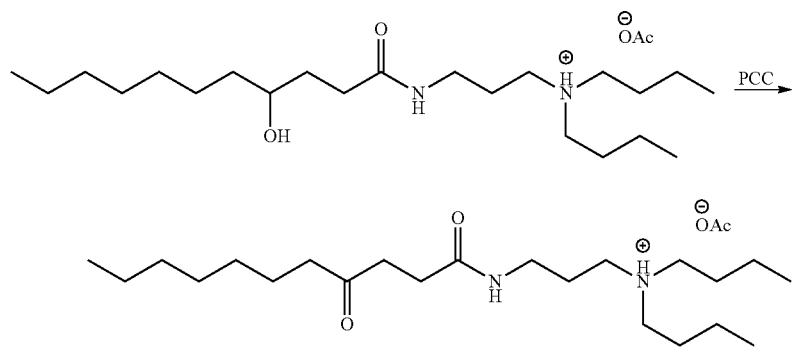

tone, whisky lactone, omega-pentadecalactone, and 6-pentyl-5,6-dihydropyran-2-massoia lactone.

Any suitable amine may be used to react with the alkyl lactone. The amine may be characterized by the presence of at least of at least one primary, secondary or tertiary amino group. Suitable amine includes monoamines, diamines or polyamines.

Examples of suitable monoamines include ethylamine, dimethylamine, diethylamine, n-butylamine, dibutylamine, allylamine, isobutylamine, cocoamine, stearylamine, laurylamine, methyllaurylamine, oleylamine, N-methyl-octylamine, dodecyl-amine, diethanolamine, morpholine, and octadecyl amine.

In other embodiments, the amines are diamines, which can include aliphatic diamines, branched aliphatic diamines, cyclic diamines.

In embodiments, the amine dimethylaminopropyl amine.

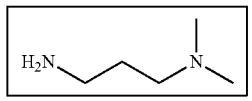

In embodiments, the amine is a dibutylaminopropylenediamine (DBAPA)

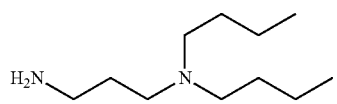

In embodiments, the polyamines have the formula [$R^5$—NH—$R^6$], wherein $R^5$ and $R^6$ are a H or an alkyl group.

In embodiments, polyamines are used in the preparation of the AA. In embodiments, polyalkylene polyamines of about 2 to 60, 2 to 40, 3 to 20 total carbon atoms and about 1 to 12, 3 to 12, 5 to 9 nitrogen atoms in the molecule.

In embodiments, amines are hydrocarbyl amines or hydrocarbyl amines including other groups, e.g., hydroxy groups, alkoxy groups, amide groups, nitriles, imidazoline groups, and the like. Hydroxy amines with 1 to 6 hydroxy groups or 1 to 3 hydroxy groups are useful.

In embodiments, amines are aliphatic saturated amines, including those of the general formulas:

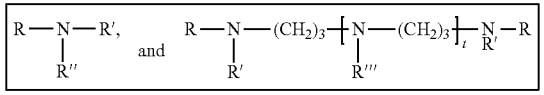

wherein R, R', R" and R'" are independently selected from a group of hydrogen; C1 to C25 straight or branched chain alkyl radicals; C1 to C12 alkoxy C2 to C6 alkylene radicals; C2 to C12 hydroxy amino alkylene radicals; and C1 to C12 alkylamino C2 to C6 alkylene radicals; and wherein R'" can additionally comprise a moiety of the formula:

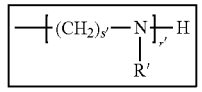

wherein R' is as defined above, and wherein s and s' can be the same or a different number of from 2 to 6, 2 to 4; and t and t' can be the same or different and are numbers of from 0 to 10, 2 to 7, or about 3 to 7, with the proviso that the sum of t and t' is not greater than 15.

In embodiments, exemplary amine compounds include: 1,2-diaminoethane; 1,3-diaminopropane; 1,4-diaminobutane; 1,6-diaminohexane: polyethylene amines such as diethylene triamine; triethylene tetramine; tetraethylene pentamine; polypropylene amines such as 1,2-propylene diamine; di-(1,2-propylene)triamine; di-(1,3-propylene) triamine; N,N-dimethyl-1,3-diaminopropane; N,N-di-(2-aminoethyl) ethylene diamine; N, N-d (2-hydroxyethy 1)-1,3-propylene diamine; 3-dodecyloxypropylamine; N-dodecyl-1,3-propane diamine; tris hydroxymethylaminomethane (THAM); diisopropanol amine; diethanol amine; triethanol amine; mono-, di-, and tri-tallow amines; amino morpholines such as N-(3-aminopropyl)morpholine; and mixtures thereof.

In embodiments, the acidification step is of a secondary or tertiary amine. In embodiments, the acidification is generally achieved through the addition of an organic acid. Exemplary organic acids include acetic acid or acrylic acid. In other embodiments, the acrylic acid reactions with any residual primary or secondary amines (reversibly with tertiary amines) to yield a carboxybetaine structure. Other organic acids may be used for this acidification, including pivalic acid, malic acid, maleic acid, succinic acid, and any C1-C12+ carboxylic acids. Inorganic acids can also be used, such as common mineral acids (hydrochloric acid, phosphoric acid, nitric acid, carbonic acid) or related, as well as Lewis acids (tetrafluoroborate, aluminum trichloride, or the like).

Any suitable alcohol may be used to react the alkyl lactone to result in the disclosed alkyl lactone-derived hydroxyester. In embodiments, alcohols having the formula: OH—$R^7$ are used, wherein $R^7$ is an alkyl, aryl or alkaryl hydrocarbyl group having from one to twenty carbons, and wherein $R^7$ may be C1-C20 unsubstituted or substituted alkyl, C2-C20 unsubstituted or substituted alkenyl, C2-C20 unsubstituted or substituted alkynyl, C3-C20 unsubstituted or substituted cycloalkyl, C3-C20 unsubstituted or substituted cycloalkyl containing at least one heteroatom, C6-C20 unsubstituted or substituted aryl, C6-C20 unsubstituted or substituted aryl containing at least one heteroatom, C7-C20 unsubstituted or substituted alkaryl, or C7-C20 unsubstituted or substituted alkaryl containing at least one heteroatom.

In embodiments, the alcohols are methanol, ethanol, propanol, i-propanol, n-butanol, butanol, t-butanol, n-octanol, hexanol, cyclohexanol and benzyl alcohol or combinations thereof. In embodiments, the alcohol is an amino alcohol. Amino alcohols include the 2,2-disubstituted-2-amino-1-alkanols having from two to three hydroxy groups and containing a total of 4 to 8 carbon atoms. This amino alcohol can be represented by the formula:

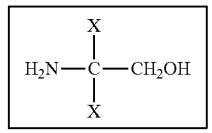

wherein X is an alkyl or hydroxyalkyl group with the alkyl groups having from 1 to 3 carbon atoms wherein at least one, and preferably both, of the X substituents is a hydroxyalkyl group of the structure —$(CH_2)_n$ OH, n being 1 to 3.

In embodiments, the alcohols are amino alcohols. Examples of amino alcohols include 2-amino-2-methyl-1,3 propanediol, 2-amino-2-ethyl-1,3-propanediol, and 2-amino-2-(hydroxymethyl)1,3-propanediol, (THAM or tris (hydroxymethyl) amino methane). In other embodiments, the alcohol is a dibutylaminoethanol, diethylaminoethanol, dipropylaminoethanol, diisopropyl, diisobutyl, diisopentyl, dipentyl and diisohexyl/dihexyl.

The compositions and methods described herein are used to inhibit corrosion. In embodiments, compositions comprise, consist essentially of, or consist of at least one of the described alkyl lactone-derived hydroxyamides or alkyl lactone-derived hydroxyester used for corrosion inhibition. In embodiments, the alkyl lactone-derived hydroxyamides or alkyl lactone-derived hydroxyesters or compositions containing them include other additives such as one or more asphaltene inhibitors, paraffin inhibitors, scale inhibitors, demulsifiers, water clarifiers, dispersants, emulsion breakers, antifoams, or any combination thereof. In embodiments, the alkyl lactone-derived hydroxyamide or alkyl lactone-derived hydroxyester further comprises one or more solvents or a mixture thereof.

In embodiments, the solvents suitable for formulation with the alkyl lactone-derived hydroxyamide or alkyl lactone-derived hydroxyester composition are water, brine, seawater, alcohols such as methanol, ethanol, isopropanol, n-propanol, n-butanol, isobutanol, sec-butanol, t-butanol or higher alcohols such as benzyl alcohol); ketones such as acetone, or methyl ethyl ketone (2-butanone); acetonitrile; esters such as ethyl acetate, propyl acetate and butyl acetate; ethers such as diethyl ether or higher, e.g. methyl t-butyl ether, glyme, diglyme, ethylene glycol monobutyl ether, ethylene diglycol ethyl ether, 1,4 dioxane and related; aromatics such as toluene, xylene(s), diethylbenzene, naphthalene and related aromatics or refinery cuts (heavy aromatic naptha, heavy aromatic distillates, and related); aliphatics such as pentane, hexane, heptane, octane, or refined gasoline; or several "green" solvents such as 2-methyltetrahydrofuran, furfural alcohol, and cyclopentylmethylether.

In embodiments, the solvents suitable for formulation with the alkyl lactone-derived hydroxyamide or alkyl lactone-derived hydroxyester composition are aliphatic, such as pentane, hexane, cyclohexane, methylcyclohexane, heptane, decane, dodecane, diesel, and the like, and aromatics, such as toluene, xylene, heavy aromatic naphtha, fatty acid derivatives (acids, esters, amides), and the like.

In embodiments, the composition can include solvents disclosed in U.S. patent application Ser. No. 15/992,383 filed May 30, 2018.

In embodiments, the alkyl lactone-derived hydroxyamide or alkyl lactone-derived hydroxyester alone or in a composition is used in an amount from about 1 ppm to 10,000 ppm, from about 100 ppm to about 1000, from about 500 ppm to about 3000 ppm, from 750 ppm to 3,000 ppm, from about 5000 ppm to about 2,000 ppm, from about 5000 ppm to about 3,000 ppm, or 100 ppm to 3,000 ppm.

In embodiments, the composition comprising the alkyl lactone-derived hydroxyamide or alkyl lactone-derived hydroxyester is used in a method of inhibiting corrosion in a fluid source. The fluid source can be contained in a metal container or in contact with pipelines used to transport fluid sources toward, into, out of a subterranean formation. In embodiments, the corrodents include hydrogen sulfide, carbon dioxide, oxygen, sodium chloride, calcium chloride, sulfur dioxide, or combination thereof. In embodiments, the fluid source comprises water, gas, and optionally liquid hydrocarbon or combination thereof. In embodiments, the fluid source is produced water or an injectate.

In embodiments, various dosage amounts of the composition and/or the alkyl lactone-derived hydroxyamide or alkyl lactone-derived hydroxyester are introduced to a fluid source to inhibit corrosion of a metal containment in contact with the fluid source. One of ordinary skill in the art is able to calculate the amount of alkyl lactone-derived hydroxyamide or alkyl lactone-derived hydroxyester or composition comprising alkyl lactone-derived hydroxyamide or alkyl lactone-derived hydroxyester for a given situation without undue experimentation. Factors that would be considered important in such calculations include, for example, content of fluid source, content of corrodents, percentage water cut, and similar parameters.

In some embodiments, the composition comprising the alkyl lactone-derived hydroxyamide or alkyl lactone-derived hydroxyester is applied to a fluid source that contains various levels of water cut. One of ordinary skill in the art understands that "water cut" refers to the % of water in an oil and water mixture. In one embodiment, the water cut is from about 1% to about 80% w/w with respect to the hydrocarbon phase. In other embodiments, the water cut is from about 1% to about 30% w/w, from about 5% to about 40% w/w, from about 10% to about 60% w/w, from about 15% to about 80% w/w with respect to the hydrocarbon phase.

In embodiments, the composition comprising the alkyl lactone-derived hydroxyamide or alkyl lactone-derived hydroxyester is applied to a fluid source that contains various levels of salinity. In one embodiment, the fluid source has a salinity of about 0.1% to about 25% or about 10% to about 25% weight/weight (w/w) total dissolved solids.

The alkyl lactone-derived hydroxyamide or alkyl lactone-derived hydroxyester may be introduced into a fluid source by any means suitable for ensuring dispersal of the alkyl lactone-derived hydroxyamide or alkyl lactone-derived hydroxyester through the fluid source being treated. The composition comprising the alkyl lactone-derived hydroxyamide or alkyl lactone-derived hydroxyester can be injected as prepared or formulated in one or more additional solvents, depending upon the application and requirements. One of skill in the art will understand that the methods disclosed herein are not limited in any way by the timing or location of the introduction.

In embodiments, the alkyl lactone-derived hydroxyamide or alkyl lactone-derived hydroxyester are introduced to a fluid using various well-known methods and they may be introduced at numerous, different locations throughout a given system. In one embodiment, the composition comprising the alkyl lactone-derived hydroxyamide or alkyl lactone-derived hydroxyester is pumped into an oil/gas pipeline using an umbilical line. In some embodiments, capillary string injection systems may be utilized to deliver the composition. U.S. Pat. No. 7,311,144 provides a description of an apparatus and methods relating to capillary injection, the disclosure of which is incorporated into the present application in its entirety. In other embodiments, the composition comprising the one or more alkyl lactone-derived hydroxyamide or alkyl lactone-derived hydroxyester is injected using mechanical equipment such as chemical injection pumps, piping tees, injection fittings, and the like.

Introducing may be achieved also by mixing, blending with mechanical mixing equipment or devices, stationary mixing setup or equipment, magnetic mixing or other suitable methods, other equipment and means known to one skilled in the art and combinations thereof to provide adequate contact and/or dispersion of the composition into the fluid source. The contacting can be made in-line and/or offline. The various components of the composition may be mixed prior to and/or during contact. If needed or desired, the composition or some of its components may be optionally removed or separated mechanically, chemically, or by other methods known to one skilled in the art.

In embodiments, the alkyl lactone-derived hydroxyamide or alkyl lactone-derived hydroxyester described herein have increased biodegradation, lower toxicity, lower bioaccumulation or combination thereof. In embodiments, the alkyl lactone-derived hydroxyamide or alkyl lactone-derived hydroxyester have a biodegradation of greater than 10%, greater than 20%, greater than 30%, greater than 40%, greater than 50% or greater than 60% when measured in a 28 day degradation test.

In embodiments, the alkyl lactone-derived hydroxyamide or alkyl lactone-derived hydroxyester have reduced toxicity as measured in a 48 hour acute toxicity test with *Daphnia magna*. In embodiments, the alkyl lactone-derived hydroxyamide or alkyl lactone-derived hydroxyester has a 48-hour $EC_5 0$ value with *Daphnia magna* of greater than or equal to 10 mg/ml. In embodiments, the alkyl lactone-derived hydroxyamide or alkyl lactone-derived hydroxyester has a 48-hour $EC_5 0$ value with *Daphnia magna* from about 10-100 mg/ml, 10-20 mg/ml, 15-25 mg/ml, 20-35 mg/ml, 30-40 mg/ml, 35-50 mg/ml, 40-60 mg/ml, 50-80 mg/ml, 60-90 mg/ml, or 70-100 mg/ml.

Some additional non-limiting embodiments are provided below to further exemplify the present disclosure:

Embodiment 1: A composition comprising at least one alkyl lactone-derived hydroxyamide or alkyl lactone-derived hydroxyester to inhibit corrosion, the at least one alkyl lactone-derived hydroxyamide formed by a reaction between an alkyl lactone with an amine, and the alkyl lactone-derived hydroxyester formed by a reaction between an alkyl lactone with an alcohol.

Embodiment 2: The composition of embodiment 1, wherein the alkyl lactone comprises a 2 to 30 carbon atom-containing lactone.

Embodiment 3: The composition as in one of embodiments 1-2, wherein the alkyl lactone comprises a 1-30 carbon atom-containing alkyl substituent.

Embodiment 4: The composition of embodiment 1, wherein the alkyl lactone is a δ undecalactone, a γ undecalactone or a γ octalactone.

Embodiment 5: The composition as in one of embodiments 1-4, wherein the amine comprises a primary, secondary or tertiary amine.

Embodiment 6: The composition as in one of embodiments 1-5, wherein the amine is a dimethylaminopropylamine.

Embodiment 7: The composition as in one of embodiments 1-6, wherein the alkyl lactone-derived hydroxyamide comprises:

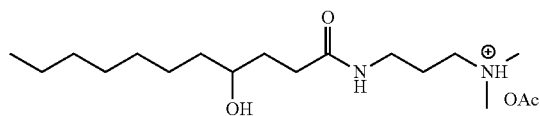

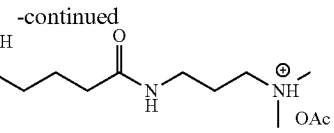

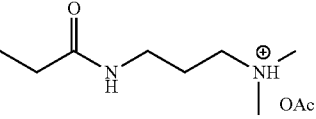

Embodiment 8: The composition as in one of embodiments 1-4, wherein the alcohol is an amino alcohol.

Embodiment 9: The composition as in one of embodiments 1-8, wherein the composition further comprises one or more asphaltene inhibitors, paraffin inhibitors, scale inhibitors, emulsifiers, water clarifiers, dispersants, emulsion breakers, or any combination thereof.

Embodiment 10: The composition as in one of embodiments 1-9, wherein the alkyl lactone-derived hydroxyamide or alkyl lactone-derived hydroxyester comprises a reduced toxicity compared to compositions not containing alkyl lactone derived hydroxyamide or alkyl lactone-derived hydroxyester.

Embodiment 11: The composition as in one of embodiments 1-10, wherein the alkyl lactone derived hydroxyamide or alkyl lactone-derived hydroxyester comprises a $EC_5 0$ value with *Daphnia magna* greater than or equal to 10 mg/ml.

Embodiment 12: The composition as in one of embodiments 1-11, wherein the alkyl lactone derived hydroxyamide or alkyl lactone-derived hydroxyester comprises a 48-hour $EC_5 0$ value with *Daphnia magna* from about 10-100 mg/ml.

Embodiment 13: The composition as in one of embodiments 1-12, wherein the alkyl lactone derived hydroxyamide or alkyl lactone-derived hydroxyester has an increased biodegradation compared to non-alkyl lactone-derived corrosion inhibitors.

Embodiment 14: The composition as in one of embodiments 1-13, wherein the composition has biodegradation of greater than 10%, greater than 20%, greater than 30%, greater than 40%, greater than 50%, or greater than 60% when measured in a 28 day degradation test.

Embodiment 15: A composition comprising:
A fluid source; and
the alkyl lactone-derived hydroxyamide or alkyl lactone-derived hydroxyester composition as in one of embodiments 1-14.

Embodiment 16: The composition as in one of embodiments 1-17, wherein the the alkyl lactone-derived hydroxyamide or alkyl lactone-derived hydroxyester is about is about 1 ppm to 10,000 ppm by weight.

Embodiment 17: The composition as in one of embodiments 15-17, wherein the fluid source is produced water or injectate.

Embodiment 18: The composition as in one of embodiments 15-18, wherein the fluid source comprises water, gas, and optionally liquid hydrocarbon.

Embodiment 19: A method of inhibiting corrosion of metal containments in contact with a fluid source comprising the steps of:
introducing into the fluid source a composition comprising at least one alkyl lactone-derived hydroxyamide or alkyl lactone-derived hydroxyester, the at least one alkyl lactone-derived hydroxyamide formed by a reaction between an alkyl lactone with an amine, and the at lease one alkyl lactone-derived hydroxyester formed by a reaction between an alkyl lactone with an alcohol.

Embodiment 20: The method of embodiment 19, wherein introducing is by injecting or pumping.

Embodiment 21: The method as in one of embodiments 19-20, wherein the fluid source is contained in an oil or gas pipeline or refinery.

Embodiment 22: The method as in one of embodiments 19-21, wherein the fluid source comprises water, gas, optionally liquid hydrocarbon or combination thereof.

Embodiment 23: The method as in one of embodiments 19-22, wherein the fluid source comprises about 0.1% to about 25% weight/weight total dissolved solids.

Embodiment 24: The method as in one of embodiments 19-23, wherein the fluid comprises water of about 1% to about 80% weight/weight with respect to the hydrocarbon phase.

Embodiment 25: The method as in one of embodiments 19-24, wherein the alkyl lactone comprises a 2 to 30 carbon atom-containing lactone.

Embodiment 26: The method as in one of embodiments 19-25, wherein the alkyl lactone comprises a 1-30 carbon atom-containing alkyl substituent.

Embodiment 27: The method as in one of embodiments 19-26, wherein the alkyl lactone is a δ undecalactone, γ undecalactone or a γ octalactone.

Embodiment 28: The method as in one of embodiments 19-27, wherein the amine comprises a dimethyl aminopropylamine.

Embodiment 29: The method as in one of embodiments 19-28, wherein the reaction product comprises:

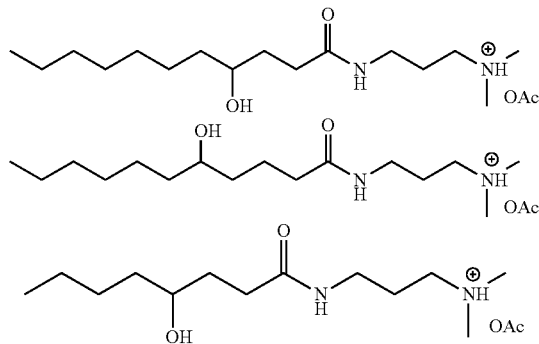

Embodiment 30: The method as in one of embodiments 19-27, wherein the alcohol is an amino alcohol.

Embodiment 31: The method as in one of embodiments 19-30, wherein the alkyl lactone-derived hydroxyamide or alkyl lactone-derived hydroxyester has the general formula:

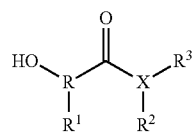

wherein X=nitrogen or oxygen;
wherein $R^1$=any fatty tail derived from 1-30 carbon saturated or unsaturated alkyl group or a ring structure including cyclohexyl, cyclopentyl, phenyl, benzyl, or variants thereof;

wherein $R^2$=is H or any 1-10 carbon saturated or unsaturated alkyl group or a ring structure which would link to $R^3$; and wherein $R^3$=H or any 1-10 carbon saturated or unsaturated alkyl group or a ring structure which would link to $R^2$.

Embodiment 32: Use of the alkyl lactone-derived hydroxyamide or alkyl lactone-derived hydroxyester as in one of embodiments 1-31 to inhibit corrosion.

EXAMPLES

The following examples are intended to illustrate different aspects and embodiments of the invention and are not to be considered limiting the scope of the invention. It will be recognized that various modifications and changes may be made without following the experimental embodiments described herein, further without departing from the scope of the claims.

Example 1

γ-Undecalactone/DMAPA

In a 40 mL, Teflon top vial was weighed 5.0 g of γ-undecalactone and 2.77 g of dimethylaminopropylamine (1 eq). A stir bar was added and the flask was set to stir at 50° C. for 4 hours. Once the reaction was complete, the contents were allowed to return to room temperature and 1.62 g acetic acid (1.0 eq) was added to the contents. Finally, the contents were diluted to 50 wt % active in methanol.

δ-Undecalactone/DMAPA

In a 40 mL, Teflon top vial was weighed 5.0 g of δ-undecalactone and 2.77 g of dimethylaminopropylamine (1 eq). A stir bar was added and the flask was set to stir at 50° C. for 4 hours. Once the reaction was complete, the contents were allowed to return to room temperature and 1.62 g acetic acid (1.0 eq) was added. Finally, the contents were diluted to 50 wt % active in methanol.

γ-Octalactone/DMAPA

In a 40 mL, Teflon top vial was weighed 2.0 g of γ-octalactone and 1.437 g of dimethylaminopropylamine (1 eq). A stir bar was added and the flask was set to stir at 50° C. for 4 hours. Once the reaction was complete, the contents were allowed to return to room temperature and 0.845 g acetic acid (1.0 eq) was added to the contents. Finally, the contents were diluted to 50 wt % active in methanol.

Example 2

The bubble cell test was used to investigate the effectiveness of alkyl lactone-derived hydroxyamides as corrosion inhibitors. This test measures the corrosion rate of a steel electrode by aqueous linear polarization resistance (LPR). The steel electrodes (C1018) were placed in a bath of synthetic oilfield brine which was deaerated with carbon dioxide. The corrosion rate of the electrode was compared in the absence or presence of an alkyl lactone-derived hydroxyamide.

The synthetic oilfield brine contained about 3 wt % of sodium chloride, and the oil included a synthetic oil of LVT-200 and xylene. The ratio of water to oil was 80:20. The oil/brine was placed into bubble cells and purged with $CO_2$. The oil/brine was continually purged with $CO_2$ to saturate the oil/brine prior to starting the test. The test cells were blanketed with $CO_2$ throughout the duration of the test to maintain saturation. The bubble cells were stirred at 100 revolutions per minute (rpm) for the duration of the test to maintain thermal equilibrium at 80° C. The electrodes were all cleaned and polished prior to testing. Details of the test are shown in Table 1.

TABLE 1

Test Conditions

| | |
|---|---|
| Temperature (° C.) | 80 |
| Water Cut (%) | 80 |
| Oil Type | 75% LVT-200, Xylene 25% |
| Stirrer Speed (rpm) | 100 |
| Purge Gas | CO2 |
| $CO_2$ pressure | Ambient |
| $H_2S$ (ppm) | 0 |
| Electrode Material | C1018 |

After about 3 hours of pre-corrosion time (i.e. without a corrosion inhibitor) 10 ppm of a 20% active of an alkyl-lactone chemistry (shown in Table 2 and prepared as described in Example 1) with 2% 2-mercaptoethanol (2ME) solvent was added. Comparison with a benzyl ammonium chloride quaternary chemistry and imidazoline chemistry was made at the same active concentration as the alkly lactone together with 2ME (at the same dose based on chemistry and 2ME activity—i.e. these were dosed at twice the concentration because the active and 2ME in the test blend was half).

The bubble cells were dosed with the various samples shown in Table 2.

TABLE 2

| Sample | Chemistry |
|---|---|
| Blank | brine and synthetic oil without a corrosion inhibitor |
| Comparative sample A | standard benzyl ammonium chloride quaternary chemistry |
| Comparative sample B | TOFA:DETA imidazoline salted with acetic acid |
| Sample 1 | γ undecalactone + dimethylaminopropyl amine (DMAPA) conjugate + acetic acid. |

TABLE 2-continued

| Sample | Chemistry |
|---|---|
| Sample 2 | δ undecalactone + dimethylaminopropyl amine (DMAPA) conjugate + acetic acid |
| Sample 3 | γ octalactone + dimethylaminopropyl amine (DMAPA) conjugate + acetic acid. |

The results are shown in Table 3. In the presence of the same concentration of both active chemistry and synergist, the resultant hydroxyamide, which is a reaction between δ undecalactone, dimethylaminopropyl amine (DMAPA)+ acetic acid chemistry (Sample 2) outperformed the standard benzyl ammonium chloride quaternary chemistry (Comparative Sample A) in which a 43% corrosion inhibition was gained for Sample 2 compared with 38% inhibition for Comparative Sample A. Sample 2 provided similar performance to the standard imidazo line chemistry, which also provided a 43% inhibition.

Sample 1 and Sample 3 showed similar results as the Comparative Sample A.

TABLE 3

| | | | | | 15 h after dosing | | |
|---|---|---|---|---|---|---|---|
| Chemical | Candidate Chemistry | Synergist | Candidate Chemistry Activity (%) | Dosage (ppm) | Baseline Corrosion Rate (mpy) | Inhibited Corrosion Rate (mpy) | % Protection |
| Blank | N/A | N/A | N/A | 0 | 260 | 500 | −92 |
| Comparative sample A | Dimethyl benzyl ammonium chloride quaternary (% n-Alkyl (5% C12, 60% C14, 30% C16, 5% C18) | 1% 2ME | 10 | 20 | 236 | 147 | 38 |
| Comparative sample B | TOFA:DETA imidazoline salted with acetic acid | 1% 2ME | 10 | 20 | 245 | 141 | 43 |
| Sample 1 | γ undecalactone/ DMAPA + acetic acid | 2% 2ME | 20 | 10 | 289 | 181 | 37 |
| Sample 2 | δ undecalactone/ DMAPA + acetic acid | 2% 2ME | 20 | 10 | 266 | 151 | 43 |
| Sample 3 | γ octalactone/ DMAPA) + acetic acid | 2% 2ME | 20 | 10 | 255 | 177 | 31 |

What is claimed is:

1. A composition comprising
   an alkyl lactone-derived hydroxyamide formed by a reaction between an alkyl lactone with N,N dimethylpropane-1,3-diamine,
   wherein the alkyl lactone is selected from one or more of gamma-undecalactone, delta-undecalactone, and gamma-octalactone.

2. The composition of claim 1, the composition comprising the alkyl lactone derived hydroxyamide selected from the group consisting of:
   a compound having the structure

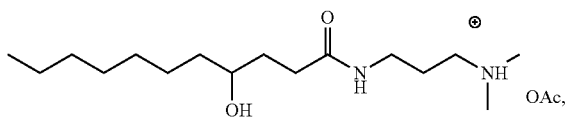 [SMILES: CCCCCCCC(O)CCC(=O)NCCCN(C)C]

a compound having the structure

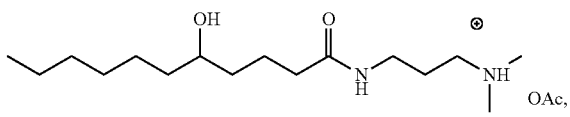 [SMILES: CCCCCCC(O)CCCC(=O)NCCCN(C)C]

a compound having the structure

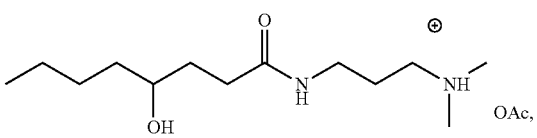 [SMILES: CCCCC(O)CCC(=O)NCCCN(C)C]

and any combination thereof.

3. The composition of claim 1, wherein the composition further comprises one or more asphaltene inhibitors, paraffin inhibitors, scale inhibitors, emulsifiers, water clarifiers, dispersants, emulsion breakers, or any combination thereof.

4. The composition of claim 1, wherein the composition comprising the alkyl lactone-derived hydroxyamide comprises a reduced toxicity compared to compositions not containing alkyl lactone derived hydroxyamide.

5. The composition of claim 1, wherein the alkyl lactone derived hydroxyamide comprises a $EC_5 0$ value with *Daphnia magna* greater than or equal to 10 mg/ml.

6. The composition of claim 1, wherein the alkyl lactone derived hydroxyamide comprises a 48-hour $EC_5 0$ value with *Daphnia magna* from about 10-100 mg/ml.

7. The composition of claim 1, wherein the alkyl lactone derived hydroxyamide has an increased biodegradation compared to non-alkyl lactone-derived corrosion inhibitors.

8. The composition of claim 1, the composition further comprising a fluid source, wherein the fluid source comprises a liquid hydrocarbon, gas, or a combination thereof.

9. The composition of claim 1, wherein the alkyl lactone-derived hydroxyamide is acidified.

10. The composition of claim 1, the composition further comprising produced water, the produced water comprising residual hydrocarbon products entrained therein and one or more of injectate, connate, brackish water, and sea water.

11. The composition of claim 1, the composition further comprising an injectate.

12. The composition of claim 8, wherein the fluid source comprises one or more of hydrogen sulfide, carbon dioxide, oxygen, sodium chloride, calcium chloride, and sulfur dioxide.

13. A composition comprising an alkyl lactone-derived hydroxyester to inhibit corrosion, the alkyl lactone-derived hydroxyester formed by a reaction between an alkyl lactone and an alcohol having the structure

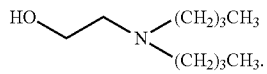

14. The composition of claim 13, wherein the composition further comprises one or more asphaltene inhibitors, paraffin inhibitors, scale inhibitors, emulsifiers, water clarifiers, dispersants, emulsion breakers, or any combination thereof.

15. The composition of claim 13, wherein the composition comprising the alkyl lactone-derived hydroxyester comprises a reduced toxicity compared to compositions not containing alkyl lactone-derived hydroxyester.

16. The composition of claim 13, wherein the alkyl lactone-derived hydroxyester comprises a $EC_5 0$ value with *Daphnia magna* greater than or equal to 10 mg/ml.

17. The composition of claim 13, wherein the alkyl lactone-derived hydroxyester comprises a 48-hour $EC_5 0$ value with *Daphnia magna* from about 10-100 mg/ml.

18. The composition of claim 13, wherein the alkyl lactone-derived hydroxyester has an increased biodegradation compared to non-alkyl lactone-derived corrosion inhibitors.

19. The composition of claim 13, the composition further comprising a fluid source, wherein the fluid source comprises water, gas, liquid hydrocarbon, or any combination thereof.

20. The composition of claim 13, wherein the alkyl lactone is gamma-undecalactone.

* * * * *